United States Patent
Lundqvist et al.

(10) Patent No.: US 10,614,547 B2
(45) Date of Patent: Apr. 7, 2020

(54) METHODS OF SPATIAL NORMALIZATION OF POSITRON EMISSION TOMOGRAPHY IMAGES

(71) Applicant: GE HEALTHCARE LIMITED, Buckinghamshire (GB)

(72) Inventors: Roger Lundqvist, Uppsala (SE); Nils Lennart Thurfjell, Uppsala (SE); Johan Lilja, Uppsala (SE)

(73) Assignee: GE HEALTHCARE LIMITED, Buckinghamshire (GB)

(*) Notice: Subject to any disclaimer, the term of this patent is extended or adjusted under 35 U.S.C. 154(b) by 0 days.

(21) Appl. No.: 14/344,934

(22) PCT Filed: Sep. 20, 2012

(86) PCT No.: PCT/US2012/056182
§ 371 (c)(1),
(2) Date: Mar. 14, 2014

(87) PCT Pub. No.: WO2013/043775
PCT Pub. Date: Mar. 28, 2013

(65) Prior Publication Data
US 2014/0350392 A1    Nov. 27, 2014

Related U.S. Application Data

(60) Provisional application No. 61/536,702, filed on Sep. 20, 2011.

(51) Int. Cl.
*G06T 3/00* (2006.01)
*A61B 6/03* (2006.01)
(Continued)

(52) U.S. Cl.
CPC ............ *G06T 3/0068* (2013.01); *A61B 6/037* (2013.01); *A61B 6/501* (2013.01); *A61B 6/5217* (2013.01);
(Continued)

(58) Field of Classification Search
CPC .............................. A61B 6/032; A61B 6/504
See application file for complete search history.

(56) References Cited

U.S. PATENT DOCUMENTS

| | | | | |
|---|---|---|---|---|
| 5,948,384 A | * | 9/1999 | Filler | A61K 9/0024 424/1.11 |
| 2010/0049032 A1 | * | 2/2010 | Steinke | G01R 33/481 600/416 |

(Continued)

FOREIGN PATENT DOCUMENTS

| | | |
|---|---|---|
| EP | 2126609 B1 | 3/2013 |
| JP | 2006-320387 A | 11/2006 |

(Continued)

OTHER PUBLICATIONS

Fripp J. et. al., "Generative Atlases and Atlas Selection for C11-PIB-PET-PET Registration of Elderly, Mild Cognitive Impaired and Alzheimer Disease Patients," Biomedical Imaging: From Nano to Macro, 2008. ISBI 2008. 5th IEEE International Symposium. May 14, 2008, pp. 1155-1158.*

(Continued)

*Primary Examiner* — Hien N Nguyen
(74) *Attorney, Agent, or Firm* — Hanley, Flight and Zimmerman, LLC

(57) ABSTRACT

An adaptive template image for registering a PET or a SPECT image includes a template image model including variability of values for each voxel in a template image according to one or more control parameters.

15 Claims, 6 Drawing Sheets

(51) Int. Cl.
*A61B 6/00* (2006.01)
*G06T 7/33* (2017.01)

(52) U.S. Cl.
CPC .... *G06T 7/337* (2017.01); *G06T 2207/10104* (2013.01); *G06T 2207/10108* (2013.01); *G06T 2207/20004* (2013.01); *G06T 2207/30016* (2013.01)

(56) References Cited

U.S. PATENT DOCUMENTS

| | | |
|---|---|---|
| 2010/0080432 A1 | 4/2010 | Lilja et al. |
| 2010/0221181 A1* | 9/2010 | Thiele ................ A61K 51/0455 424/1.85 |
| 2011/0160543 A1* | 6/2011 | Parsey .................. A61B 5/055 600/300 |

FOREIGN PATENT DOCUMENTS

| | | |
|---|---|---|
| JP | 2010-517030 A | 5/2010 |
| WO | 2008/093057 | 8/2008 |

OTHER PUBLICATIONS

Fripp, et.al. Biomedical Imaging: From Nano to Macro, 2008, p. 1155-1158.
PCT/US2012/056182 ISRWO dated Feb. 13, 2013.

* cited by examiner

Typical patterns of Flutemetamol uptake in Aβ + (top row) and Aβ − scans (bottom row). It can be seen that there is considerably more uptake in gray matter in the Aβ + scan.

Outline of extended spatial normalization method.

SUVR mean values for Aβ- and Aβ+ subjects measured inside a composite region defined as an average of the SUVR values in the prefrontal cortex, parietal cortex, precuneus, lateral temporal cortex, and the anterior and posterior cingulate cortices. Pons was used as reference region for the calaulation of SUVR values.

Intercept image (top row) and slope image (bottom row) from linear regression of input images on $COM_{SUVR}$ values. Images are shown as an overlay on top of the MR Tl template image.

Template images showing typical Flutemetamol patterns going from fully normal Aβ- (upper left) to severely Aβ+ (lower right).
The value of x is increased in steps by 0.2 going from left to right.

METHODS OF SPATIAL NORMALIZATION OF POSITRON EMISSION TOMOGRAPHY IMAGES

This application is a filing under 35 U.S.C. 371 of international application number PCT/US2012/056182, filed Sep. 20, 2012, which claims priority to U.S. application No. 61/536,702 filed Sep. 20, 2011, the entire disclosure of which is hereby incorporated by reference.

FIELD OF THE INVENTION

The present invention relates to the field of positron emission tomography (PET) image analysis and single photon emission tomography (SPECT). More specifically, the present invention relates to a method of spatial normalization of PET and SPECT images.

BACKGROUND OF THE INVENTION

When making automated inter-individual quantitative analysis from PET and SPECT imaging data it is important to have a robust and accurate spatial normalization method, which can be used to transform images from different individuals into a common reference space where comparisons between individuals can be made. This means that different organ images, for example brain images, are transformed into a standard anatomical space in which the organs from different individuals have the same position, size and shape, so as to allow for comparison across different individuals. This is relevant for both volume-of-interest (VOI) analysis as well as voxel-based analysis from imaging data.

For spatial normalization of PET and SPECT images, either the individual PET/SPECT image or a co-registered anatomical image may be used to find the spatial transformation between an individual image and a template image located in the reference space. In most applications, the use of anatomical information will enhance the possibility of making a good spatial normalization. However, there is a trade-off in making a method dependent on an anatomical image. For instance when there is no anatomical image available, the options would either be to disallow the analysis completely, or to use an alternative PET/SPECT-based method which would produce different results.

There is therefore a need in the art for a spatial normalization method specifically for PET and SPECT images, such as images using amyloid imaging agents, which only depends on the PET or SPECT image itself.

SUMMARY OF THE INVENTION

In view of the needs of the prior art, the present invention provides a model-controlled adaptive template image integrated with a spatial normalization method. The present invention may be applied to imaging agents such as, by way of illustration and not of limitation, amyloid imaging agents.

In one embodiment, the present invention provides an adaptive template image for registering a PET image, the adaptive template image includes a template image model wherein the values for each voxel in a template image vary (ie, have a variability) according to one or more control parameters.

In another embodiment, the present invention is tuned to the specific problem of registering imaging data from patients with Alzheimer's Disease (AD), MCI, as well as individuals expressing a normal uptake pattern, a high uptake pattern, or a low uptake pattern.

In one embodiment, the variability of values for each voxel ranges between a value corresponding to the normal level of uptake of an imaging agent and an abnormal level of uptake of the imaging agent.

For example, the level of uptake of the imaging agent may be indicate/be detected for the grey matter of the brain. The abnormal level of uptake may result from a relatively high level of uptake or a relatively low level of uptake of the imaging agent.

In another embodiment, the variability of values for each voxel ranges between a value corresponding to a normal level of amyloid in grey matter and a high amyloid level in grey matter. It is further contemplated that the imaging agent may be [$^{18}$F]Flutemetamol (Flutemetamol), where high levels of uptake in gray matter are indicative of high levels of amyloid. In is also contemplated that the imaging agent could be DaTSCAN®, sold by GE Healthcare of Amersham, U.K., where low levels of uptake in the striatum are indicative of low levels of dopamine transport.

In another embodiment, the present invention provides a method of registering a PET or SPECT image to an adaptive template image comprising the steps of:

Spatially normalizing an individual PET image to an adaptive template image located in the reference space;

Comparing the spatially normalized individual PET image to the adaptive template image to determine whether both are sufficiently converged; and Altering the parameter controlling the template image and the parameters controlling the spatial transformation for the individual PET image so as render an altered template image and an updated spatially transformed individual PET image in the event that the comparing step does not determine that the spatially normalized individual PET image is sufficiently converged to the adaptive template image.

In a further embodiment, the present invention provides a method of constructing an adaptive template comprising the steps of:

Calculating a mean image from a set of input PET/SPECT images showing uptake of an imaging agent in a region of interest, the set of input PET/SPECT images having been transformed into a reference space; and Calculating a regression model for each voxel in a set of images having been transformed into a reference space, where the dependent variable represents the voxel intensities in the input images and is regressed on some variable which for each input image represents a "true" value of where on a scale from a normal level of uptake to a high level of uptake of the imaging agent the voxel is located.

The present invention further provides non-transitory computer readable storage medium comprising computer readable program code including instructions for registering a PET image to an adaptive template image, wherein execution of the computer readable program code causes a processor to carry out the steps of the method of registering a PET image to an adaptive template image of the present invention.

The present invention still further provides a non-transitory computer readable storage medium comprising computer readable program code including instructions for using an adaptive template the present invention.

The present invention even further provides A system for registering a PET image to an adaptive template comprising:
means for transforming a moving image using selected start parameters;
a source for a template model;

means for modifying the template model using a control parameter so as to provide an adaptive template;

means for comparing the transformed moving image with the adaptive template;

means for selecting new parameters to apply to the transformed image and a new control parameter for the adaptive template;

means for transforming the transformed moving image using the new parameters;

means for adjusting the adaptive template using the new template control parameter; and means for storing the transformed moving image when it has sufficiently converged with the adaptive template.

The present invention even still further provides a positron emission tomography (PET) system comprising:

a storage device;

a detector for detecting positron emissions from a brain of a subject, wherein the detector generates signals representing the positron emissions that are stored in the storage device;

an image processor for, wherein the image processor is programmed to:

Spatially normalize an individual PET image to an adaptive template image located in the reference space;

Compare the spatially normalized individual PET image to the adaptive template image to determine whether both are sufficiently converged; and Alter the parameter controlling the template image and the parameters controlling the spatial transformation for the individual PET image so as render an altered template image and an updated spatially transformed individual PET image in the event that the comparing step does not determine that the spatially normalized individual PET image is sufficiently converged to the adaptive template image.

This system is further contemplated to include a display for displaying an image of the brain based on the SSP data set.

The present invention even yet further provides a positron emission tomography (PET) system comprising:

an image processor for registering a PET image to an adaptive template image that is programmed to:

Spatially normalize an individual PET image to an adaptive template image located in the reference space;

Compare the spatially normalized individual PET image to the adaptive template image to determine whether both are sufficiently converged; and Alter the parameter controlling the template image and the parameters controlling the spatial transformation for the individual PET image so as render an altered template image and an updated spatially transformed individual PET image in the event that the comparing step does not determine that the spatially normalized individual PET image is sufficiently converged to the adaptive template image.

The present invention even still yet further provides a computer-implemented method of registering a registering a PET image to an adaptive template image, the method comprising:

Spatially normalizing an individual PET image to an adaptive template image located in the reference space;

Comparing the spatially normalized individual PET image to the adaptive template image to determine whether both are sufficiently converged; and Altering the parameter controlling the template image and the parameters controlling the spatial transformation for the individual PET image so as render an altered template image and an updated spatially transformed individual PET image in the event that the comparing step does not determine that the spatially normalized individual PET image is sufficiently converged to the adaptive template image.

The present invention also still further provides a computer-implemented method of constructing an adaptive template comprising the steps of:

Calculating a mean image from a set of input PET images showing uptake of an imaging agent in a region of interest, the set of input PET images having been transformed into a reference space; and Calculating a regression model for each voxel in the set of images having been transformed into a reference space, where the dependent variable represents the voxel intensities in the input images and is regressed on some variable which for each input image represents a "true" value of where on a scale from a normal level of uptake to a high level of uptake of the imaging agent the voxel is located.

DETAILED DESCRIPTION OF THE PREFERRED EMBODIMENTS

The present invention provides a spatial normalization method when using imaging agents. While a specific embodiment for scans with the [$^{18}$F]-Flutemetamol amyloid imaging agent, which only depends on the Flutemetamol scan itself, are described in detail, the present invention is also applicable to other imaging agents used for other imaging applications. For example, the present invention may also be employed for DaTSCAN imaging where low uptake in the brain is indicative of disease.

The uptake pattern in Flutemetamol scans can differ much between normal subjects (Aβ−) and subjects with high amyloid in gray matter (Aβ+). Therefore the spatial normalization method has been extended with an adaptive template mechanism, which during the image registration process alters the template image along with the spatial transformation parameters to make it more similar to the scan being registered. By using this extension, the method can accurately spatially normalize scans ranging over the whole amyloid scale from Aβ− to very high Aβ+.

The present invention solves this by creating a model over how the typical uptake pattern in the whole image varies along the scale going from Aβ− to Aβ+. In the model presented hereinbelow, a one parameter linear regression model for each voxel in the image is used to express the dependence, but generally a more advanced model expressing uptake pattern dependence on multiple parameters, is also contemplated by the present invention. The model is built once for all in a separate pre-processing step and is then fixed as an internal part of the method. Although the method described below has been developed for Flutemetamol it should be noted that other PET amyloid tracers exhibit exactly the same characteristic. Moreover, the method described is general and there is nothing limiting the method of the present invention to PET amyloid scans only. As long as a model over the typical variation modes of the images being registered can be created, the adaptive template method has potential to be used for other imaging agents as well as for both PET and SPECT applications. While the examples provided hereinbelow are directed PET applications, the present invention also applies to SPECT applications.

Figure 1:
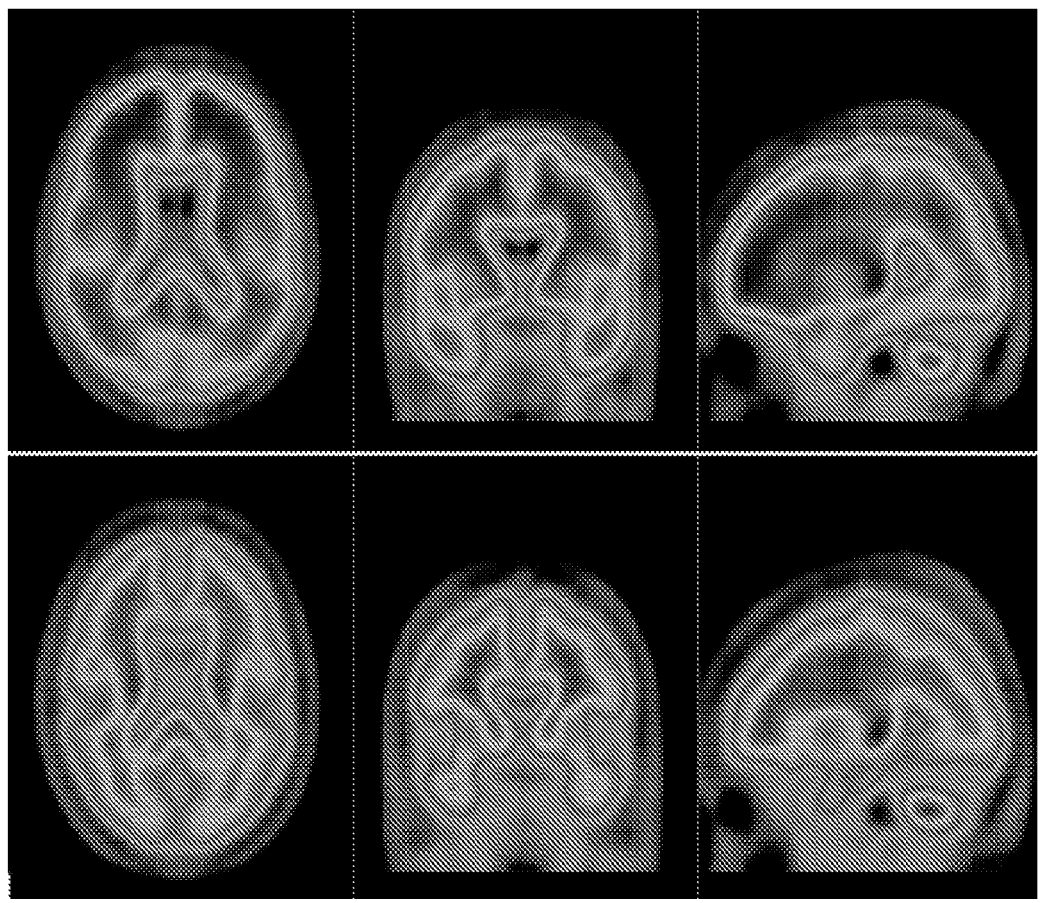
FIG. 1 provides an illustration of typical Flutemetamol uptake patterns in an amyloid positive (Aβ+) and amyloid negative (Aβ−) scan.

As noted hereinabove, the present invention may alter one or more of the parameters for the image, the image template, or both. For example, parameters for spatial transformation may include translation along each axis (providing three possible parameters), scaling along each axis (providing another three possible parameters), and rotation about each axis (providing an additional three parameters), for a total of up to nine parameters which may be altered by the present invention. Additionally, parameters which account for shape differences between the image and the adaptive template provide additional parameters which may be altered by the present invention An illustration of typical Flutemetamol uptake patterns in an Aβ+ and Aβ− scan is shown in FIG. 1. It can be noted that the Aβ+ have much more activity in cortical gray matter and even though white matter activity is about the same in the two cases the relative activity pattern between white and gray matter is to some extent reversed. That is from having highest activity in white matter in Aβ− to the opposite with highest, or at least as high, activity in gray matter in Aβ+.

Spatial normalization is the process of transforming a scan from patient space to a standard space thus allowing for comparison of data from different subjects. Typically this is performed through an iterative process where the patient scan is compared with a template image and where it is geometrically transformed to be as similar to the template as possible. However, by observing the patterns above it can be seen that there is no obvious way of selecting a similarity metric for a spatial normalization method which would be able to perform accurate and robust registrations of both of these types of images, by comparing them to a common template image.

Figure 2:
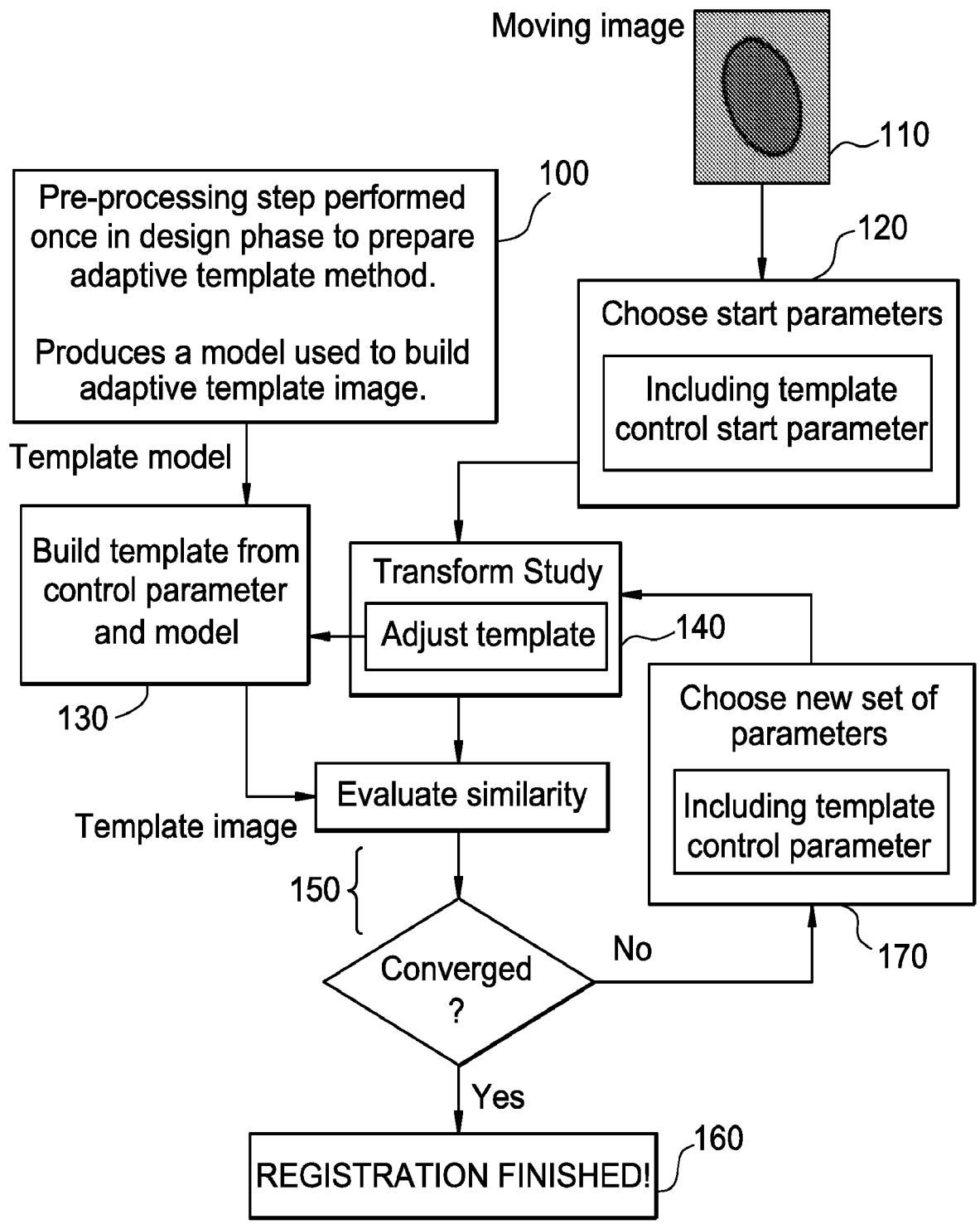
FIG. 2 depicts an outline of the complete image registration procedure including the novel extension.

Therefore, the present invention provides an extension to be used together with a standard image registration method, where the number of possible template images is infinite. Basically, no definite selection of one specific template image occurs. Instead the intensities in the template are continuously altered during the registration, to make the template converge along with the spatial transformation parameters, to optimally fit the image being registered. An outline of the complete image registration procedure including the novel extension is shown in FIG. 2.

First, the step of providing a template model 100 is performed. Step 100 is a pre-processing step performed once during a design phase to prepare the adaptive template of the present invention. Separately, a moving image (ie, the patient image) 110, such as a PET or SPECT scan, is taken of a subject and the step of choosing starting parameters 120 for the moving image is performed. Including within step 120 is the step of choosing a template control start parameter. In short the following steps are then iterated until convergence is reached. An adaptive template is then built 130 using the control parameter for the adaptive template and the model from step 100. A transforming step 140 is performed in which the moving image is adjusted using the start parameters. Then, a comparison step 150 is performed which compares the similarity between the transformed moving image and the adaptive template. In this step, the similarity metric is evaluated from the voxel values in the template image and the transformed moving image. If the moving image and the adaptive template are found to be sufficiently or maximally converged, the registration of the moving image is completed, step 160. Should the moving image and the adaptive template not be sufficiently or maximally converged, the step of choosing new parameters 170, for both the moving image and the template control parameter, is performed. Then transforming step 140 is repeated, this time using the parameters chosen during step 170. Additionally, step 130 is repeated in which the existing adaptive template is also modified by the new template control parameter chosen during step 170. The comparison step 150 is again performed using the newly transformed moving image and adaptive temple. If the method has not converged, another set of adaptive template and transformation parameters is selected by the optimization method and a new evaluation of the similarity metric is made. The present invention contemplates that the optimization method may be any numerical optimization method.

Convergence may be sufficiently achieved when the value of a function for describing the similarity between the images has reached a level deemed suitable for proceeding. Convergence is desirably achieved when the value of a function for describing the similarity between the images has reached its maximum, ie, showing maximum similarity between the template image in reference space and the transformed image. The similarity metric could be based, for example, on correlation or on mutual information, although the present invention contemplates that any suitable similarity metric may be applied.

The pre-processing step 100 is performed once and the extra parameter or parameters controlling the template model are added to the registration parameters and altered by the optimization method in a similar way as the parameters controlling the geometry change. The following will now in detail describe the creation of a one-parameter linear template model, which has been found to be suitable for Flutemetamol PET scans.

The present invention is contemplated to provide a non-transitory computer-readable storage medium with an executable program for performing the method of the present invention. This computer-readable storage medium includes computer-readable program code includes instructions for performing a method of the present invention, such that execution of the computer-readable program code causes a processor to perform the steps of the method of the present invention. Additionally, the present invention is contemplated to use an adaptive template model of the present invention for performing the spatial normalization method of the present invention. The starting parameters may be fixed for all procedures and the updated parameters may be selected automatically by the process.

Adaptive Template Image Model

In the following example, Montreal Neurological Institute (MNI) reference space sampled to a uniform 2×2×2 mm voxel size is used as standard space for the template image. A set of Flutemetamol input images is provided to create a template of the present invention, which images have already have been spatially normalized to this space using an MR-based spatial normalization method.

Normally when creating a template image for spatial normalization one takes these spatially-normalized input images and calculates a mean image from these. It follows that this mean image will also be located in the reference space and can be used for spatial normalization of new unseen images by using an image registration method to find the transformation making the new images match the template mean image.

However, as described hereinabove, the problem with this approach is that the mean image will only be representative for one typical image pattern for a specific level of amyloid, i.e. either the pattern of a Aβ−, Aβ+, or something in between. To be able to create a model of the image pattern variability the present invention instead calculates a regression model for each voxel in the template image, where the dependent variable which is the voxel intensities in the input images is regressed on some variable which ideally for each input image expresses a "true" value of where on a scale from Aβ− to very severe Aβ+ it is located.

In practice, it is impossible to extract such true values but, being principally interested in finding a robust estimated value for each scan on a one-dimensional scale of how much Aβ the gray matter contains, this approach provides such a robust estimate. Therefore the present invention calculates for all input images a mean standard uptake ratio value (SUVR) inside a large composite region (COM) covering regions known to be most affected by Aβ in Alzheimer's disease patients. These regions were the prefrontal cortex, parietal cortex, precuneus, lateral temporal cortex, and the anterior and posterior cingulate cortices.

Figure 3:
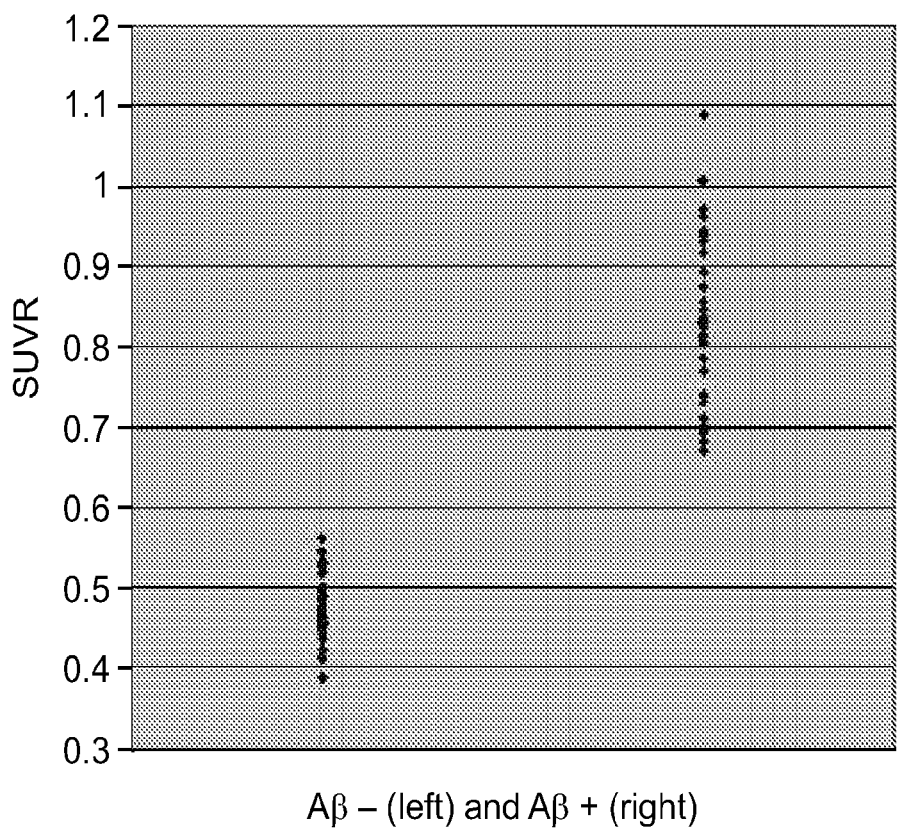
FIG. 3 depicts an illustration of the calculated mean SUVR values of the composite region $COM_{SUVR}$ for all subjects in two different groups of Aβ− and Aβ+ scans.

An illustration of the calculated SUVR values of the composite region $COM_{SUVR}$ for all subjects in two different groups of Aβ− and Aβ+ scans is shown in FIG. 3.

It is thus seen that the present invention uses a good sampling over the whole spectrum from Aβ− subjects with very low Flutemetamol uptake inside COM to Aβ+ subjects with a very high Flutemetamol uptake.

In the next step, the linear regression model was applied for each voxel i in the template image matrix to express the dependence of that particular voxel, $y_i$, on the $COM_{SUVR}$ values according to Equation 1:

$$y_i = \hat{\alpha}_i + \hat{\beta}_i COM_{SUVR} + \varepsilon_i \quad \text{Equation 1}$$

Linear regression model

Applying this model over all input images regressed on the corresponding $COM_{SUVR}$ values provides an intercept image and a slope image according to Equation 2:

$$I_0 = [\hat{\alpha}_1 \; \hat{\alpha}_2 \ldots \hat{\alpha}_n]$$

$$I_{Slope} = [\hat{\beta}_1 \; \hat{\beta}_2 \ldots \hat{\beta}_n] \quad \text{Equation 2}$$

Intercept image, $I_0$, and slope image, $I_{Slope}$, created from linear regression, where n is the number of voxels in the images.

Figure 4:
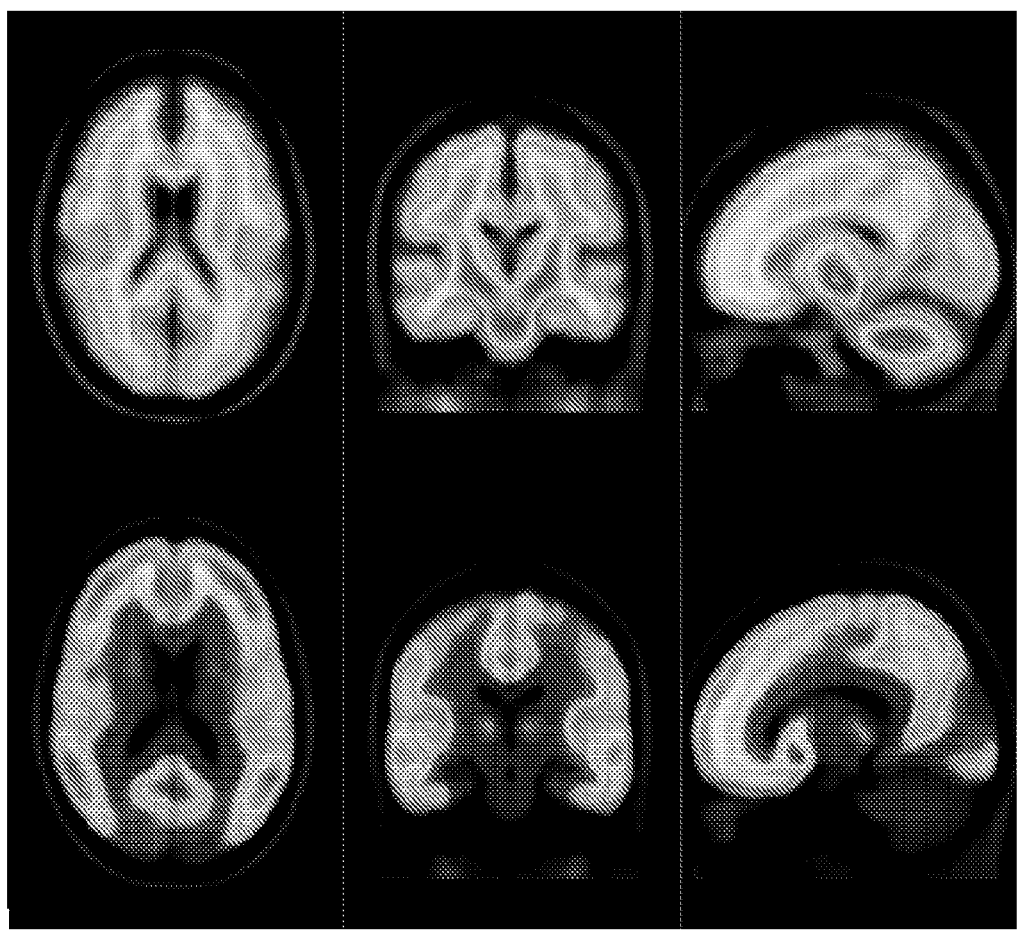
FIG. 4 depicts the resulting slope and intercept images according to one embodiment of the present invention.

The intercept image will correspond to a pattern of a fully normal subject located in the lower part of the $COM_{SUVR}$ scale. The slope image, on the other hand, will have the highest values for the parts of the image where the largest changes occur when going from low to high on the $COM_{SUVR}$ scale. These resulting images are shown in FIG. 4.

From these images the present invention creates synthetic simulated images, along the whole $COM_{SUVR}$ scale over the range from Aβ− to Aβ+. This is done by adding multiplicatively scaled portions of $I_{Slope}$ to $I_0$ according to Equation 3:

$$I_{template} = I_0 + I_{slope} \, x \quad \text{Equation 3}$$

Template image equation

Figure 5:
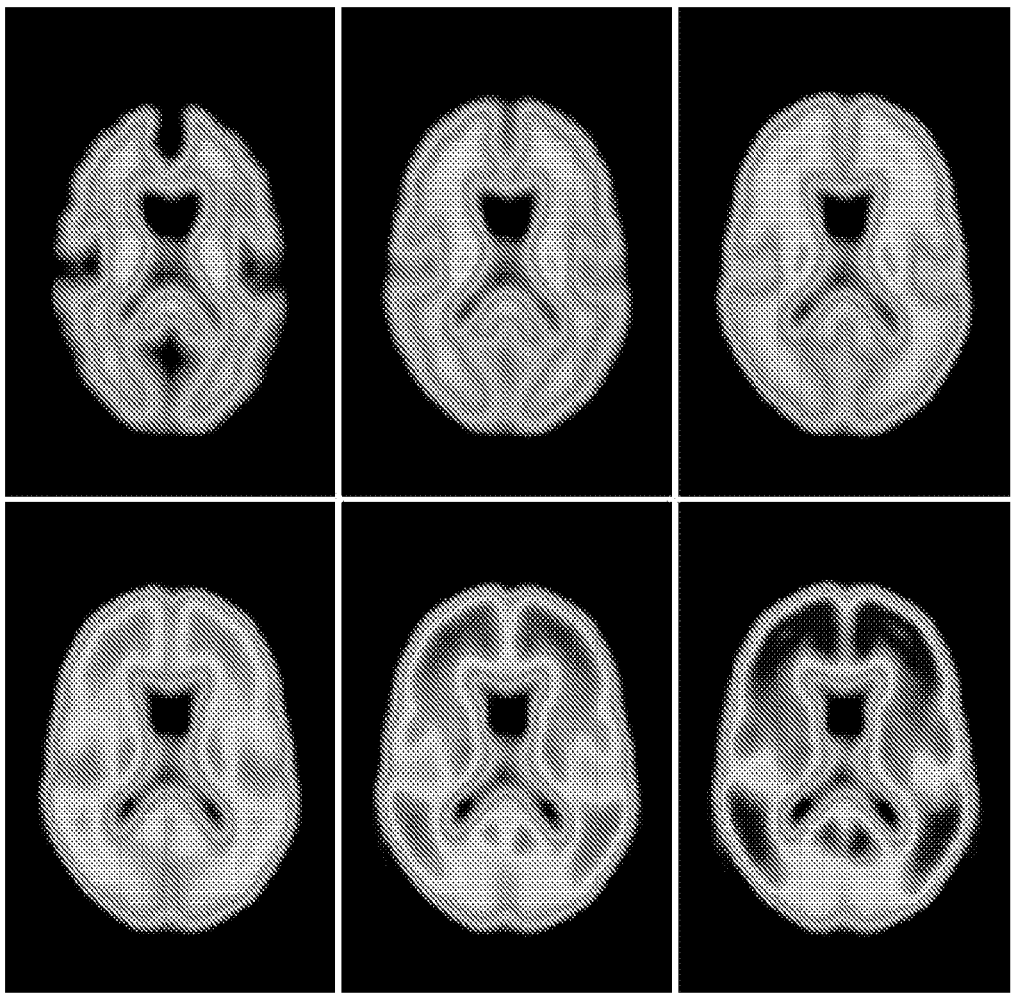
FIG. 5 shows template images of the present invention.

A value of the scale factor x of 0.0 will correspond to $I_0$ itself, which represents a pattern of an Aβ− subject, and a value of 1.0 will correspond to an Aβ+ subject in the high end of the $COM_{SUVR}$ scale. From this formula the present invention can create synthetic images for any x along the linear path defined by $I_{Slope}$. FIG. 5 shows such synthetic images covering values of x from 0.0 to 1.0 in steps of 0.2.

Such synthetic images are used as the adaptive template in a spatial normalization method. The slope image, $I_{Slope}$, and intercept image, $I_0$, is the adaptive template model is controlled by one single parameter x. This parameter x is then adjusted by the image registration algorithm in a similar way as any of the other parameters, and the template image is updated accordingly any time the x parameter is changed.

Figure 6:
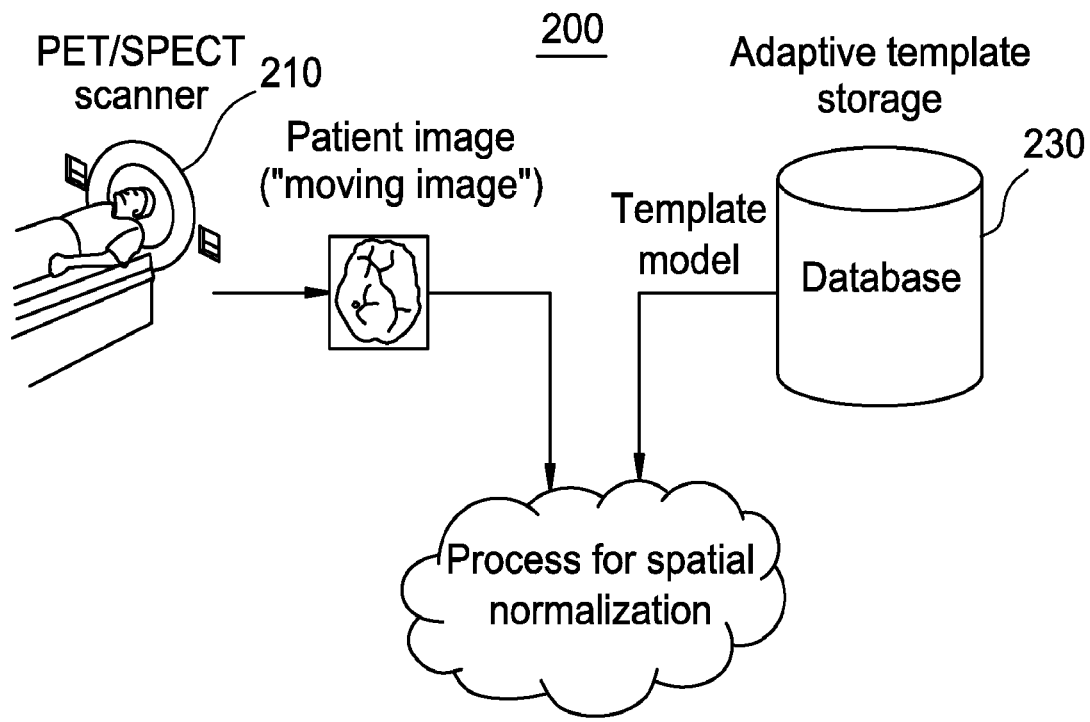
FIG. 6 depicts a system for performing the instant invention.
Figure 6:
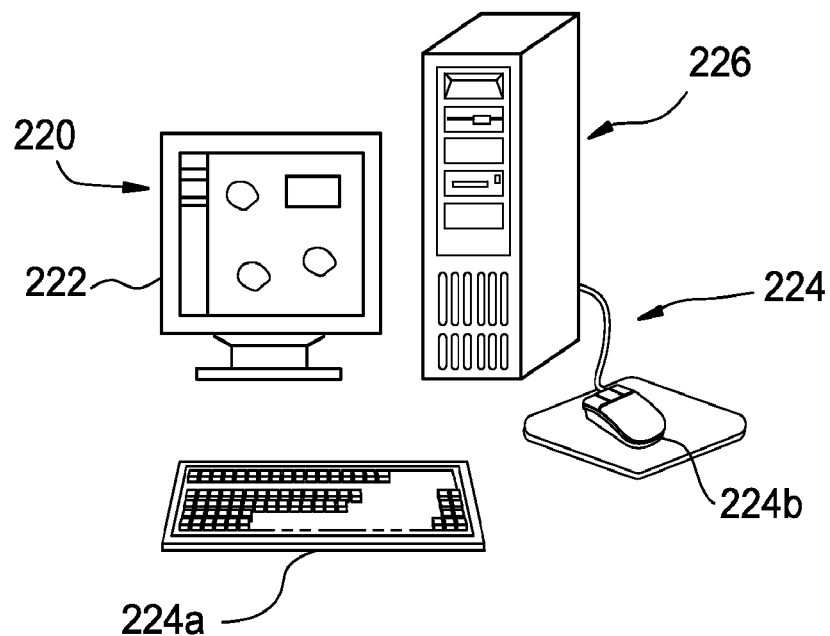

Referring now to FIG. 6, the method of the present invention is contemplated to be performed by system 200. System 200 includes a scanner 210 for performing PET or SPECT scans, a computer 220 for receiving scan images, e.g, the patient image (aka, the moving image), and a database 230 for providing the adaptive template. Computer 220 typically includes a display 222, an input device 224 such as a keyboard 224a and a mouse 224b, and a processor 226. Processor 226 typically includes software for performing the method of the instant invention using the adaptive template from database 230 and the moving image from scanner 210. Additionally, processor 226 is contemplated to include non-transitory computer readable storage medium with an executable program for using an adaptive template of the present invention and for registering a PET image to an adaptive template image according to a method of the instant invention using the moving image from scanner 210. The non-transitory computer readable storage medium includes computer-readable program code including instructions for using an adaptive template of the present invention and for registering a PET image to an adaptive template image. Connections between scanner 210, computer 220, and database 230 are contemplated to be by any means known to the art, such as hardwire, wireless, or any combination thereof. Additionally, the present invention contemplates that processor 226 and database 230 are connected such that processor 226 may return the upgraded adaptive template to database 230 upon completion of the method of the present invention.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. An adaptive template image system configured to perform spatial normalization and registration of a PET or a SPECT image using a single image registration procedure, the system comprising:

a storage configured to store and provide an adaptive template image comprising a template image model including a variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering the PET or the SPECT image in the reference space during the single image registration procedure; and an image processor configured to at least:
  initiate a first registration of the PET or SPECT image into the reference space;
  spatially normalize the PET or SPECT image to the adaptive template image in the first registration by:
    (i) adjusting the template image model using a first control parameter, the adjusting to include adjusting among the variability of values for one or more voxels in the adaptive template image based on the first control parameter,
    (ii) rendering the adaptive template image from the template image model,
    (iii) performing a spatial normalization operation by adjusting the PET or SPECT image using spatial transformation parameters,
    (iv) evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and
    (v) when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation at (iv) within the single registration procedure and without performing the image registration until the adaptive template image converges to fit the PET or SPECT image; and
  when the adaptive template image converges to fit the PET or SPECT image, register the PET or SPECT image in the reference space to complete the first registration.

2. The adaptive template image system of claim 1, wherein the level of uptake is measured in gray matter of a brain.

3. The adaptive template image system of claim 1, wherein the variability of values for each voxel ranges from a value corresponding to a normal level of amyloid in grey matter to a raised amyloid level in grey matter.

4. The adaptive template image system of claim 1, wherein the control parameter is selected as part of a spatial normalization optimization process.

5. The adaptive template image system of claim 1, wherein $I_0$ and $I_{slope}$ are determined using regression analysis of multiple images spanning different levels of disease state.

6. A method of performing spatial normalization of a PET or a SPECT image, using a single image registration procedure, and of registering the PET or the SPECT image to an adaptive template image comprising a template image model comprising variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering the PET or the SPECT image in the reference space during the single image registration procedure, the method comprising:
  initiating a first registration of the PET or SPECT image into the reference space;
  spatially normalizing the PET or SPECT image to the adaptive template image in the first registration by:
    adjusting the template image model using a first control parameter, the adjusting to include adjusting among the variability of values for one or more voxels in the adaptive template image based on the first control parameter;
    rendering the adaptive template image from the template image model;
    performing a spatial normalization operation by adjusting the PET or SPECT image using spatial transformation parameters;
    evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and
    when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation within the single registration procedure and without performing the image registration until the adaptive template image converges to fit the PET or SPECT image; and
  when the adaptive template image converges to fit the PET or SPECT image, registering the PET or SPECT image in the reference space to complete the first registration.

7. The method of claim 6, wherein said spatial normalization further comprises performing linear and non-linear transformations on the PET or SPECT image to find a match between the template image model and the PET or SPECT image, and wherein said linear transformation comprising at least one of translation, rotation, and scaling.

8. A system for performing spatial normalization of a PET or a SPECT image using a single image registration procedure, and for registering the PET or the SPECT image to an adaptive template image comprising a template image model including a variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering the PET or the SPECT image in the reference space during the single image registration procedure, the system configured to:

during a first registration of the PET or SPECT image into the reference space, spatially normalize the PET or SPECT image to the adaptive template image in the first registration by:

adjusting the template image model using a first control parameter, the adjusting to include adjusting among the variability of values for one or more voxels in the adaptive template image based on the first control parameter, rendering the adaptive template image from the template image model, performing a spatial normalization operation by adjusting the PET or SPECT image using spatial transformation parameters, evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation within the single registration procedure and without performing the image registration until the adaptive template image converges to fit the PET or SPECT image; and when the adaptive template image converges to fit the PET or SPECT image, register the PET or SPECT image in the reference space to complete the first registration.

9. A non-transitory computer readable storage medium comprising computer readable program code including instructions for performing spatial normalization of a PET or a SPECT image, using a single image registration procedure, and for registering the PET or the SPECT image to an adaptive template image comprising a template image model comprising variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering the PET or the SPECT image in the reference space during the single image registration procedure, wherein execution of the computer readable program code causes a processor to carry out a method comprising:

initiating a first registration of the PET or SPECT image into the reference space;

spatially normalizing the PET or SPECT image to the adaptive template image in the first registration by:

adjusting the template image model using a first control parameter, the adjusting to include adjusting among the variability of values for one or more voxels in the adaptive template image based on the first control parameter;

rendering the adaptive template image from the template image model;

performing a spatial normalization operation by adjusting the PET or SPECT image using spatial transformation parameters;

evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation within the single registration procedure and without performing the image registration until the adaptive template image converges to fit the PET or SPECT image; and when the adaptive template image converges to fit the PET or SPECT image, registering the PET or SPECT image in the reference space to complete the first registration.

10. A method of constructing an adaptive template image comprising a template image model including a variability of values for one or more voxels in the adaptive template image, the method comprising:

transforming a set of PET or SPECT images into a reference space using spatial transformation parameters;

calculating a regression model for each voxel in the set of PET or SPECT images having been transformed into the reference space, where a dependent variable represents voxel intensities in the set of PET or SPECT images and is regressed on some variable which for each input PET or SPECT image represents a "true" value of where on a scale from a normal level of uptake to a high level of uptake of an imaging agent the voxel is located; and generating, based on the template image model and a control parameter, the adaptive template image for registering, in a single registration procedure, the PET or SPECT image, wherein the PET or SPECT image is to be registered by at least:

spatially normalizing, in a first registration of the PET or SPECT image into the reference space, the PET or SPECT image to the adaptive template image in the first registration by:

adjusting the template image model using a first control parameter x, the adjusting to include adjusting among the variability of values for one or more voxels in the adaptive template image based on the first control parameter x, wherein the variability of values for each voxel ranges from a value corresponding to a normal level of uptake of an imaging agent to an abnormal level of uptake of the imaging agent, and wherein the imaging agent includes amyloid imaging agent and a level of uptake is determined for a striatum, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the first control parameter x, rendering the adaptive template image from the adjusted template image model, performing a spatial normalization operation by adjusting the PET or SPECT image using spatial transformation parameters, evaluating the adaptive template image and the PET or SPECT image to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation within the single registration procedure and without performing the image registration until the adaptive template image converges to fit the PET or SPECT image; and when the adaptive template image converges to fit the PET or SPECT image, registering the PET or SPECT image in the reference space to complete the first registration.

11. The method of claim 10, wherein the normal level of uptake corresponds to Aß− and the high level of uptake corresponds to Aß+.

12. The method of claim 10, wherein the set of PET or SPECT images have been transformed into the reference space with a co-registered anatomical image.

13. A positron emission tomography (PET) system comprising:

a storage device configured to store and provide an adaptive template image comprising a template image model including a variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering a PET or a SPECT image in the reference space during single image registration procedure;

a detector for detecting positron emissions from a brain of a subject, wherein the detector generates signals representing the positron emissions that are stored in the storage device;

an image processor configured to at least:
initiate a first registration of the PET or SPECT image into the reference space;
spatially normalize the PET or SPECT image to the adaptive template image in the first registration by:

(i) adjusting the template image model using a first control parameter, the adjusting to include adjusting among the variability of values for one or more voxels in the adaptive template image based on the first control parameter, (ii) rendering the adaptive template image from the template image model, (iii) performing a spatial normalization operation by adjusting the PET or SPECT image using spatial transformation parameters, (iv) evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and (v) when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation at (iv) within the single registration procedure and without performing the image registration until the adaptive template image converges to fit the PET or SPECT image; and when the adaptive template image converges to fit the PET or SPECT image, register the PET or SPECT image in the reference space to complete the first registration.

14. A positron emission tomography (PET) system comprising:

an image processor for performing spatial normalization and registration of a PET or a SPECT image, using a single image registration procedure, and for registering the PET the SPECT image to an adaptive template image comprising a template image model including a variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering the PET or the SPECT image in the reference space during the single image registration procedure, the image processor configured to:

initiate a first registration of the PET or SPECT image into the reference space;

spatially normalize the PET or SPECT image to the adaptive template image in the first registration by:

adjusting the template image model using a first control parameter, the adjusting to include adjusting among the variability of values for one or more voxels in the adaptive template image based on the first control parameter;

rendering the adaptive template image from the template image model;

performing a spatial normalization operation by adjusting the PET or SPECT image using spatial transformation parameters;

evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and when the adaptive template image does not converge to fit the PET or SPECT image, continuously and adaptively altering both the adaptive template image and the PET or SPECT image by selecting an updated control parameter to render the adaptive template image and updated spatial transformation parameters to spatially normalize the PET or SPECT image for re-evaluation within the single registration procedure and without performing the image registration until the adaptive template image converges to fit the PET or SPECT image; and when the adaptive template image converges to fit the PET or SPECT image, register the PET or SPECT image in the reference space to complete the first registration.

15. A computer-implemented method of performing spatial normalization of a PET or a SPECT image, using a single image registration procedure, and registering of the PET or the SPECT image to an adaptive template image comprising a template image model including a variability of values for one or more voxels in the adaptive template image, wherein the variability of values for each voxel ranges from a value corresponding to a normal level of uptake of an imaging agent to an abnormal level of uptake of the imaging agent, and wherein the imaging agent includes a dopamine transport agent DaTSCAN and a level of uptake is determined for a striatum, the variability of values adjustable using a control parameter x, wherein the values of the voxels are defined by an equation:

$$I^i_{template} = I^i_0 + I^i_{slope} x,$$

and wherein $I^i_{template}$ is the value of the voxel i in the adaptive template image, $I^i_0$ represents a value corresponding to a normal level of uptake of the imaging agent within that voxel, $I^i_{slope}$ corresponds to a maximum additional amount of uptake of the imaging agent corresponding to a high level uptake of the imaging agent in that voxel with respect to the control parameter x, wherein the adaptive template image is in a reference space and is used for registering the PET or the SPECT image in the reference space during the single image registration procedure, the method comprising:

initiating a first registration of the PET or SPECT image into the reference space;

spatially normalizing the PET or SPECT image to the adaptive template image in the first registration by:

adjusting the template image model using a first control parameter, the adjusting to include adjusting among the variability of values for one or more voxels in the adaptive template image based on the first control parameter;

rendering the adaptive template image from the template image model;

performing a spatial normalization operation by adjusting the PET or SPECT image using spatial transformation parameters;

evaluating the adaptive template image and the PET or SPECT imaging to determine a convergence of the adaptive template image to the PET or SPECT image, wherein the convergence is determined by comparing voxels of the adaptive template image to corresponding voxels of the PET or SPECT image, and wherein image registration between the adaptive template image and the PET or SPECT image is not performed until the adaptive template image converges to fit the PET or SPECT image, and when the adaptive template image does not converge to fit the PET or SPECT image, continuously and adaptively altering both the adaptive template image and the PET or SPECT image by selecting an updated control parameter to render the template adaptive image and updated spatial transformation parameters to spatially normalize the PET or SPECT image for re-evaluation within the single registration procedure and without performing the image registration until the adaptive template image converges to fit the PET or SPECT image; and when the adaptive template image converges to fit the PET or SPECT image, registering the PET or SPECT image in the reference space to complete the first registration.

* * * * *